United States Patent [19]
Weidner et al.

[11] Patent Number: 6,005,132
[45] Date of Patent: Dec. 21, 1999

[54] METHOD OF PREPARING ALKOXY SILANES

[75] Inventors: Richard Weidner, Burghausen; Walter Blueml, Simbach/Inn, both of Germany

[73] Assignee: Wacker-Chemie GmbH, Munich, Germany

[21] Appl. No.: 09/194,308

[22] PCT Filed: Jul. 17, 1997

[86] PCT No.: PCT/EP97/03837

§ 371 Date: Nov. 24, 1998

§ 102(e) Date: Nov. 24, 1998

[87] PCT Pub. No.: WO98/03514

PCT Pub. Date: Jan. 29, 1998

[30] Foreign Application Priority Data

Jul. 23, 1996 [DE] Germany .......................... 196 29 760

[51] Int. Cl.⁶ ...................................................... C07F 7/02
[52] U.S. Cl. ........................... 556/469; 556/470; 556/483

[58] Field of Search ..................................... 556/469, 483, 556/470

[56] References Cited

U.S. PATENT DOCUMENTS

| | | | |
|---|---|---|---|
| 2,643,263 | 6/1953 | Morgan | 260/448.8 |
| 2,917,467 | 12/1959 | Olson et al. | 260/2 |
| 4,717,773 | 1/1988 | Kenney et al. | 556/457 |

FOREIGN PATENT DOCUMENTS

| | | |
|---|---|---|
| 4040679 A1 | 6/1992 | Germany . |
| 941291 | 11/1963 | United Kingdom . |
| WO 93/16085 | 8/1993 | WIPO . |

*Primary Examiner*—Porfirio Nazario-Gonzalez
*Attorney, Agent, or Firm*—Brooks & Kushman P.C.

[57] ABSTRACT

Higher alkoxysilanes are prepared efficiently and in high yield by transesterification of lower $C_{1-4}$ alkoxysilanes with $C_{6-38}$ higher alcohols at reduced pressure with continuous removal of lower alcohol. The products have little or no lower alkoxy content, and are free of coloring impurities.

20 Claims, No Drawings

METHOD OF PREPARING ALKOXY SILANES

TECHNOLOGICAL FIELD

The invention relates to a process for the preparation of alkoxysilanes by transesterisifaction of alkoxy silanes having alkoxy radicals containing 1 to 4 carbon atoms with higher alcohols in the presence of acid or basic catalysts under a reduced pressure.

DESCRIPTION OF THE RELATED ART

U.S. Pat. No. 2,643,263 (California Research Co.; issued on Jun. 23, 1953) describes tetraalkoxysilanes which, inter alia, are prepared by reacting silicon tetrachloride with branched alcohols containing 6 to 18 carbon atoms. The preparation starting from silicon tetrachloride has the disadvantage that the products obtained show, without further involved aftertreatment, a high acidity which leads to undesired hydrolysis of the products during storage.

WO 93/16085 (Henkel KGaA; issued on Aug. 19, 1993) discloses a process for the preparation of light-coloured tetraalkoxysilanes, tetramethoxysilane or tetraethoxysilane being transesterified in a 1st step with primary higher alcohols in the presence of basic catalysts and, in a subsequent step, a neutralization and bleaching by means of solid acidic bleaching earths and cation exchangers being carried out. The 2nd step, which preferably lasts 1 to 2 hours, is necessary in this process since during the 1st step, undesirable, dark-colored tetraalkoxysilanes, which are caused by the procedure, are formed. Furthermore, the process has the disadvantage that the 1st step is very time-consuming since, caused by the procedure, the reaction mixture can be heated only at a heating rate of 0.1° to 0.5° C. per minute in order to achieve a high degree of transesterification and, furthermore, relatively high end temperatures are necessary. A further disadvantage of the process is that the transesterification takes place in a molar ratio between tetramethoxysilane or tetraethoxysilane and the primary alcohols of preferably 1:4.2 to 1:4.8 and a further expensive purification step by distillation is thus necessary due to the high boiling points.

SUMMARY OF THE INVENTION

The invention relates to a process for the preparation of alkoxysilanes having alkoxy radicals containing 6 to 38 carbon atoms by transesterification of alkoxysilanes whose alkoxy groups contain 1 to 4 carbon atoms with linear and/or branched higher alcohols containing 6 to 38 carbon atoms in the presence of basic or acid catalysts under a pressure of 1 to 800 hPa and at a temperature of 25 to 150° C. with continuous removal of the resulting alcohol containing 1 to 4 carbon atoms, the pressure and temperature during the transesterification being selected such that the higher alcohol employed and the silanes do not boil.

DESCRIPTION OF THE INVENTION

Within the scope of the present invention, the term "silanes" is intended to be understood also as mixtures of silanes and partial hydrolysis products thereof containing at most 5 silicon atoms, such partial hydrolysis products preferably being present only in small quantities such as, for example, up to 10 percent by weight, relative to the silane, or not at all.

The alkoxysilanes which are employed according to the invention and whose alkoxy groups contain 1 to 4 carbon atoms, can be any hitherto known alkoxysilanes, such as silanes having 1, 2, 3 or 4 Si-bound alkoxy groups, tetraalkoxysilanes having alkoxy groups containing 1 to 4 carbon atoms being preferred and tetramethoxysilane as well as tetraethoxysilane being particularly preferred.

The alkoxysilanes employed according to the invention can be a single species or also a mixture of at least two species of such alkoxysilanes.

The alcohols employed according to the invention are linear and/or branched alcohols which contain 6 to 38 carbon atoms and which can be aliphatically saturated or unsaturated.

Preferably, the alcohols employed according to the invention are aliphatically saturated alcohols containing 8 to 20 carbon atoms, such as 1-n-octanol, 1-n-decanol, 1-n-dodecanol, 1-n-tetradecanol and mixtures of linear and branched alcohols containing 13 to 15 carbon atoms, such as, for example, those commercially available under the designation "C13-C 15-alcohol" from BASF AG, Ludwigshafen.

The higher alcohols employed according to the invention can be a single species or also a mixture of at least two species of such alcohols.

In the process according to the invention, alkoxysilanes whose alkoxy groups contain 1 to 4 carbon atoms are employed together with higher alcohols containing 6 to 38 carbon atoms in molar quantities of preferably 1:4 to 1:4.5, particularly preferably about 1:4.

In the process according to the invention, basic and acid catalysts can be employed as the catalysts, basic catalysts being preferred.

Examples of basic catalysts are homogeneous catalysts such as, for example, alkali metal hydroxides such as sodium hydroxide and potassium hydroxide, and alkali metal alcoholates such as sodium methylate, sodium methylate being preferred.

Examples of acid catalysts are homogenous catalysts such as hydrochloric acid, sulphuric acid and p-toluene-sulphonic acid, as well as heterogeneous catalysts such as solid acid cation exchangers and solid acid-activated bleaching earths, such as, for example, those of the montmorillonite type.

The homogeneous catalysts are used in quantities of preferably 0.01 to 1.5 percent by weight, particularly preferably from 0.05 to 1 percent by weight, and the heterogeneous catalysts are preferably used in quantities of 1 to 20 percent by weight, particularly preferably from 5 to 15 percent by weight, relative to the employed alkoxysilane having alkoxy radicals containing 1 to 4 carbon atoms.

The process according to the invention is carried out at a temperature of preferably 30 to 140° C.

The process according to the invention is carried out under a pressure of preferably 5 to 300 hPa.

In the transesterification according to the invention, the pressure and temperature are to be selected such that the resulting alcohol containing 1 to 4 carbon atoms can be removed by distillation and the higher alcohol employed and the silanes do not boil. It can prove to be advantageous towards the end of the transesterification according to the invention to reduce the pressure again briefly, that is to say to lower it below the pressure selected during the tranesterification, in order completely to remove residual fractions of the alcohol formed during the tranesterification.

If homogeneous acid and basic catalysts are employed as catalysts in the process according to the invention, these are preferably neutralized after the tranesterification has taken place, and the salt formed is preferably removed by filtration. The neutralization as such has been known for a long time, it being of course possible to use the same acid and basic compounds which have been listed above also as catalysts in each case.

If heterogeneous catalysts are employed as catalysts in the process according to the invention, these are removed from the reaction mass after the transesterification has taken place—for example by filtration.

The products obtained in the process according to the invention are light-coloured, preferably colourless alkoxysilanes having alkoxy radicals containing 6 to 38 carbon atoms.

Using the process according to the invention, a degree of transesterification of from preferably 95 to 100%, particularly preferably 98 to 100%, is achieved.

The process according to the invention has the advantage that it is very simple to carry out, light-coloured, preferably colourless products being formed at a very high degree of transesterification, preferably 100%, in one process step within a relatively short time and without a further purification step.

In the examples which follow, all data of parts and percentages relate to the weight, unless otherwise stated. Unless indicated otherwise, the examples which follow are carried out under a pressure of the surrounding atmosphere, that is to say approximately under 1000 hPa, and at room temperature, that is to say at about 20° C. or at a temperature which is established when the reactants are combined at room temperature without additional heating or cooling. All viscosity data given in the examples are intended to relate to a temperature of 25° C.

The iodine colour number is determined according to DIN (Deutsche Industrie Norm—German Industiral Standard) 6162. The iodine colour number is a measure of the degree of discoloration of a product and is the quantity of iodine in mg per 100 ml of an aqueous solution whose depth of colour corresponds to that of the product to be examined in the same layer thickness.

EXAMPLE 1

179 g (0.96 mol) of 1-n-dodecanol (commercially available from Merck-Schuchardt, Hohenbrunn), 50 g (0.24 mol) of tetraethoxysilane (commercially available under the designation "TES 28" from Wacker-Chemie GmbH, Munich) and 0.5 g of a 30% solution of sodium methylate in methanol are mixed. Subsequently, the reaction mixture is heated up within 120 minutes under a pressure of 160 hPa to 130° C. and ethyl alcohol, being formed at the same time, is distilled off. The pressure is then lowered briefly to 40 hPa in order to remove residual ethyl alcohol fractions, the mixture is neutralized by the addition of 0.5 g of 20% hydrochloric acid and the resulting sodium chloride is filtered off. This gives a clear, colourless (iodine colour number=0) liquid having a viscosity of 27.5 mm$^2$/s and an HCl content of 2.5 ppm. According to $^1$H-NMR investigations, the product no longer shows any Si-ethoxy groupings nor any free ethyl alcohol.

Comparative Example 1

The procedure of Example 1 is repeated, but with the modification that the ethyl alcohol being formed during the reaction is distilled off under the pressure of the surrounding atmosphere, that is to say at about 1000 hPa. For this purpose, the reaction mixture must be heated up to 170° C. within 6 hours. The mixture is then in neutralized by the addition of 0.5 g of 20% hydrochloric acid and the resulting sodium chloride is filtered off.

This gives a clear liquid having a viscosity of 20.7 MM$^2$/s, an HCl content of 0.5 ppm and an iodine colour number of 2. According to $^1$H-NMR investigations, the product still contains 13.2 mol % of Si-ethoxy groupings and 4.4 mol % of ethanol.

EXAMPLE 2

The procedure of Example 1 is repeated, but with the modification that, in place of 179 g of 1-dodecanol, 205.9 g (0.96 mol) of a mixture comprising linear and branched primary C13-C15-alcohols (commercially available under the designation "C13-C15-alcohol" from BASF AG, Ludwigshafen) are employed.

This gives a clear colourless (iodine colour number=0) liquid having a viscosity of 37.3 mm$^2$/s and an HCl content of 3 ppm. According to $^1$H-NMR investigations, the product no longer shows any Si-ethoxy groupings nor any free ethyl alcohol.

Comparative Example 2

The procedure of Example 2 is repeated, but with the modification that ethyl alcohol being formed during the reaction is distilled off under the pressure of the surrounding atmosphere, that is to say at about 1000 hPa. For this purpose, the reaction mixture must be heated up to 160° C. within 6 hours. The pressure is then briefly lowered to 40 hPa in order to remove residual fractions of ethyl alcohol, the mixture is neutralized by the addition of 0.5 g of 20% hydrochloric acid and the resulting sodium chloride is filtered off.

This gives a clear liquid having a viscosity of 36.1 mm$^2$/s, an HCl content of 3 ppm and an iodine colour number of 1. According to $^1$H-NMR investigations, the product still contains about 0.2 mol % of Si-ethoxy groupings.

In the claims:

1. A process for the preparation of alkoxysilanes having alkoxy radicals containing 6 to 38 carbon atoms by transesterification of lower alkoxysilanes whose alkoxy groups contain 1 to 4 carbon atoms with linear, branched, or both linear and branched higher alcohols containing 6 to 38 carbon atoms in the presence of basic or acid catalysts under a pressure of 1 to 800 hPa and at a temperature of 25 to 150° C. with continuous removal of the resulting alcohol containing 1 to 4 carbon atoms, the pressure and temperature during the transesterification being selected such that the higher alcohol employed and the silanes do not boil.

2. Process according to claim 1, wherein said lower alkoxysilanes employed are tetraalkoxysilanes having alkoxy groups containing 1 to 4 carbon atoms.

3. Process according to claim 1, wherein said lower alkoxysilanes employed are tetramethoxysilane, tetraethoxysilane, or mixtures thereof.

4. Process according to claim 1, wherein said higher alcohols employed are aliphatically saturated alcohols containing 8 to 20 carbon atoms.

5. Process according to claim 1, wherein said lower alkoxysilanes whose alkoxy groups contain 1 to 4 carbon atoms are employed together with higher alcohols containing 6 to 38 carbon atoms in molar quantities of 1:4 to 1:4.5.

6. Process according to claim 1, wherein basic or acid catalysts are employed as the catalysts.

7. Process according to claim 1, wherein basic catalysts are employed.

8. Process according to claim 1, wherein said process is carried out at a temperature of 30 to 140° C.

9. Process according to claim 1, wherein said process is carried out under a pressure of 5 to 300 hPa.

10. Process according to claim 2, wherein said lower alkoxysilanes employed are tetramethoxysilane, tetraethoxysilane, or mixtures thereof.

11. Process according to claim 2, wherein said higher alcohols employed are aliphatically saturated alcohols containing 8 to 20 carbon atoms.

12. Process according to claim 3, wherein said higher alcohols employed are aliphatically saturated alcohols containing 8 to 20 carbon atoms.

13. Process according to claim 2, wherein said lower alkoxysilanes whose alkoxy groups contain 1 to 4 carbon atoms are employed together with higher alcohols containing 6 to 38 carbon atoms in molar quantities of 1:4 to 1:4.5.

14. Process according to claim 3, wherein said lower alkoxysilanes whose alkoxy groups contain 1 to 4 carbon atoms are employed together with higher alcohols containing 6 to 38 carbon atoms in molar quantities of 1:4 to 1:4.5.

15. Process according to claim 4, wherein said lower alkoxysilanes whose alkoxy groups contain 1 to 4 carbon atoms are employed together with higher alcohols containing 6 to 38 carbon atoms in molar quantities of 1:4 to 1:4.5.

16. Process according to claim 2, wherein basic or acid catalysts are employed as the catalysts.

17. Process according to claim 2, wherein basic catalysts are employed.

18. Process according to claim 2, wherein said process is carried out at a temperature of 30 to 140° C.

19. Process according to claim 2, wherein said process is carried out under a pressure of 5 to 300 hPa.

20. A process for the preparation of alkoxysilanes having alkoxy radicals containing 6 to 38 carbon atoms by transesterification of a lower alkoxysilane selected from the group consisting of tetramethoxysilane, tetraethoxysilane, and mixtures thereof, with one or more linear or branched $C_{6-38}$ aliphatic higher alcohols in a ratio of lower alkoxysilane to higher alcohol of 1:4 to 1:4.5, at a pressure of 5 to 300 hPa and a temperature of 30 to 140° C., with continuous removal of lower alcohol derived from said lower alkoxysilane, said pressure and temperature selected such that said silanes and said higher alcohol do not boil.

* * * * *

UNITED STATES PATENT AND TRADEMARK OFFICE
CERTIFICATE OF CORRECTION

PATENT NO. : 6,005,132
DATED : December 21, 1999
INVENTOR(S) : Richard Weidner, et al It is certified that error appears in the above-identified patent and that said Letters Patent is hereby corrected as shown below:

On the title page, page, item [54] and Column 1, the title should be --PROCESS FOR THE PREPARATION OF ALKOXYSILANES--.

Signed and Sealed this

Fifteenth Day of August, 2000

Attest:

Q. TODD DICKINSON

*Attesting Officer*　　　　*Director of Patents and Trademarks*